United States Patent [19]

Krämer et al.

[11] 4,415,586
[45] Nov. 15, 1983

[54] COMBATING FUNGI WITH ACYLATED IMIDAZOLYL-GAMMA-FLUOROPINACOLYL DERIVATIVES

[75] Inventors: Wolfgang Krämer, Wuppertal; Karl H. Büchel, Burscheid; Jörg Stetter, Wuppertal; Paul-Ernst Frohberger, Leverkusen; Wilhelm Brandes, Leichlingen; Volker Paul, Solingen, all of Fed. Rep. of Germany

[73] Assignee: Bayer Aktiengesellschaft, Leverkusen, Fed. Rep. of Germany

[21] Appl. No.: 376,802

[22] Filed: May 10, 1982

Related U.S. Application Data

[63] Continuation of Ser. No. 187,867, Sep. 17, 1980, abandoned.

[30] Foreign Application Priority Data

Sep. 24, 1979 [DE] Fed. Rep. of Germany ....... 2938575

[51] Int. Cl.³ ............... A01N 43/50; A01N 59/16; C07D 23/60; C07F 15/00
[52] U.S. Cl. ................ 424/273 R; 424/245; 548/101; 548/341
[58] Field of Search ............... 548/101, 341; 424/245, 424/273 R

[56] References Cited

U.S. PATENT DOCUMENTS 4,134,988  1/1979  Krämer et al. ............... 424/273 R
4,254,132  3/1981  Krämer et al. ............... 424/269
4,359,470  11/1982  Krämer et al. ............... 424/269

FOREIGN PATENT DOCUMENTS 4303   10/1979  European Pat. Off. .
6538   1/1980   European Pat. Off. .
19130  11/1980  European Pat. Off. .

2811916  9/1979   Fed. Rep. of Germany .
2918893  11/1980  Fed. Rep. of Germany ...... 548/341

Primary Examiner—Donald G. Daus
Assistant Examiner—Diana G. Rivers
Attorney, Agent, or Firm—Sprung, Horn, Kramer & Woods

[57] ABSTRACT

Fungicidally active acylated imidazolyl-γ-fluoropiniacolyl derivatives of the formula

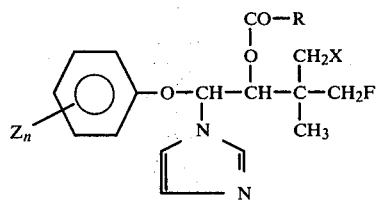

in which
R represents alkyl, alkenyl, alkynyl, alkoxy, alkoxyalkyl, cycloalkyl, halogenoalkyl, optionally substituted phenyl, optionally substituted phenylalkyl, optionally substituted phenoxyalkyl, alkylamino, dialkylamino, optionally substituted phenylamino, halogenoalkylamino, alkoxycarbonylamino or alkoxyalkylamino,
X represents hydrogen or fluorine,
Z represents halogen, alkyl, cycloalkyl, alkoxy, halogenoalkyl, alkylthio, alkoxycarbonyl, optionally substituted phenyl, optionally substituted phenoxy, optionally substituted phenylalkyl, cyano or nitro, each Z being selected independently, and
n represents 0 or an integer from 1 to 5, or a physiologically acceptable acid addition salt or metal salt complex thereof.

8 Claims, No Drawings

COMBATING FUNGI WITH ACYLATED IMIDAZOLYL-GAMMA-FLUOROPINACOLYL DERIVATIVES

This is a continuation, of application Ser. No. 187,867, filed Sept. 17, 1980 now abandoned.

The present invention relates to certain new acylated imidazolyl-γ-fluoropinacolyl derivatives, to a process for their preparation and to their use as fungicides.

It has already been disclosed that acylated 1-imidazolyl-2-hydroxy-butane derivatives, such as, in particular, 2-acyloxy- and 2-carbamoyloxy-3,3-dimethyl-1-phenoxy-1-imidazol-1-yl-butanes which are substituted in the phenyl part, have good fungicidal properties (U.S. Pat. No. 4,134,988, issued Jan. 16, 1979). However, their action is not always completely satisfactory, especially when small amounts and low concentrations are applied.

The present invention now provides, as new compounds, the acylated imidazolyl-γ-fluoropinacolyl derivatives of the general formula

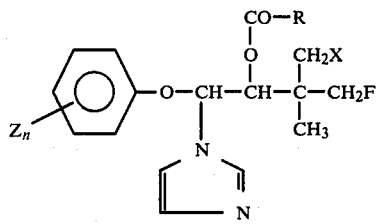

in which
- R represents alkyl, alkenyl, alkynyl, alkoxy, alkoxyalkyl, cycloalkyl, halogenoalkyl, optionally substituted phenyl, optionally substituted phenylalkyl, optionally substituted phenoxyalkyl, alkylamino, dialkylamino, optionally substituted phenylamino, halogenoalkylamino, alkoxycarbonylamino or alkoxyalkylamino,
- X represents hydrogen or fluorine,
- Z represents halogen, alkyl, cycloalkyl, alkoxy, halogenoalkyl, alkylthio, alkoxycarbonyl, optionally substituted phenyl, optionally substituted phenoxy, optionally substituted phenylalkyl, cyano or nitro, each Z being selected independently, and
- n represents 0 or an integer from 1 to 5, and physiologically acceptable acid addition salts and metal salt complexes thereof.

The compounds of the formula (I) have two asymmetric carbon atoms; they can therefore exist in the erythro-form and in the threo-form. In both cases, they exist predominantly in the form of racemates.

The invention also provides a process for the preparation of an acylated imidazolyl-γ-fluoropinacolyl derivative of the formula (I), in which a 1-imidazolyl-2-hydroxy-butane derivative of the general formula

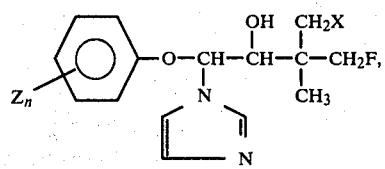

in which X, Z and n have the meanings indicated above, (a) is reacted with an acid halide of the general formula $$Hal-CO-R \qquad (III),$$

in which
R has the meaning indicated above and
Hal represents halogen, especially chlorine or bromine,
if appropriate in the presence of a solvent and if appropriate in the presence of an acid-binding agent, or (b) is reacted with an acid anhydride of the general formula $$R-CO-O-CO-R \qquad (IV),$$

in which R has the meaning indicated above, in the presence of a solvent and if appropriate in the presence of a catalyst, or (c) is reacted with a ketene of the general formula

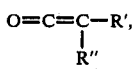

in which R' and R" are identical or different and each represent hydrogen, alkyl, alkoxy, halogen, halogenoalkyl, alkenyl or optionally substituted phenyl, in the presence of a solvent and if appropriate in the presence of a catalyst, or (d) is reacted with an isocyanate of the general formula $$O=C=N-R''' \qquad (VI),$$

in which R''' represents alkyl, halogenoalkyl, alkoxycarbonyl, alkoxyalkyl or optionally substituted phenyl, in the presence of a solvent and if appropriate in the presence of a catalyst.

Furthermore, the acylated imidazolyl-γ-fluoropinacolyl derivatives of the formula (I) which can be obtained according to the invention can be converted into salts by reaction with acids, or the corresponding metal salt complexes can be obtained by reaction with metal salts.

The present acylated imidazolyl-γ-fluoropinacolyl derivatives have powerful fungicidal properties. Surprisingly, the compounds according to the invention exhibit a considerably more powerful action than the acylated or carbamoylated imidazolyl-2-hydroxybutane derivatives which are known from the state of the art and are closely related compounds chemically and from the point of view of their action. The substances according to the invention thus represent an enrichment of the art.

The formula (I) provides a general definition of the acylated imidazolyl-γ-fluoropinacolyl derivatives according to the invention. Preferably, in this formula, R represents straight-chain or branched alkyl with 1 to 8 (especially 1 to 6) carbon atoms, straight-chain or branched alkenyl or alkynyl with in either case 2 to 4 carbon atoms, halogenoalkyl with 1 to 2 carbon atoms and 1 to 5 halogen atoms (especially fluorine and chlorine), alkoxy with 1 to 4 carbon atoms, alkoxyalkyl with 1 to 4 carbon atoms in each alkyl part, cycloalkyl with 5 to 7 carbon atoms (especially cyclohexyl), optionally substituted phenyl or phenylalkyl or phenoxyalkyl which are optionally substituted in the phenyl part and have in each case up to 2 carbon atoms in the alkyl part, the preferred substituents in the phenyl part in the last three cases being selected from halogen, cyano, nitro and alkyl and alkoxy with in either case 1 to 2 carbon atoms, or R represents alkylamino with 1 to 12 carbon atoms, dialkylamino with 1 to 4 (especially 1 or 2) carbon atoms in each alkyl part, halogenoalkylamino with up to 4 carbon atoms and up to 5 identical or different halogen atoms (especially fluorine and chlorine atoms), alkoxycarbonylamino with 1 to 4 carbon atoms in the alkyl part, alkoxyalkylamino with 1 to 4 carbon atoms in each alkyl part or optionally monosubstituted or polysubstituted phenylamino, the preferred substituents being selected from halogen, nitro, cyano, straight-chain or branched alkyl with 1 to 4 carbon atoms, alkoxy or alkylthio with in either case 1 or 2 carbon atoms, halogenoalkyl with up to 2 carbon atoms and up to 5 identical or different halogen atoms (especially fluorine and chlorine atoms) and alkoxycarbonylalkenyl with 1 to 4 carbon atoms in the alkyl part and 2 to 4 carbon atoms in the alkenyl part, X represents hydrogen or fluorine, Z represents halogen, cyano, nitro, straight-chain or branched alkyl with up to 4 carbon atoms, cycloalkyl with 5 to 7 carbon atoms (especially cyclohexyl), halogeno-alkyl with up to 2 carbon atoms and up to 5 halogen atoms (especially fluorine and chlorine atoms), alkoxycarbonyl with a total of up to 5 carbon atoms, alkoxy or alkylthio with in either case up to 2 carbon atoms or optionally substituted phenyl or phenoxy, the preferred substituents being selected from halogen, amino, cyano, nitro and alkyl with 1 to 2 carbon atoms, or Z represents optionally substituted phenylalkyl with 1 or 2 carbon atoms in the alkyl part, the preferred substituent in the alkyl part being alkylcarbonyloxy with a total of up to 3 carbon atoms, and the preferred substituents in the phenyl part being halogen, nitro and cyano, and n represents 0, 1, 2 or 3.

Very particularly preferred compounds of the formula (I) are those in which R represents methyl, ethyl, isobutyl, chloromethyl, dichloromethyl, chloroethyl, chloropropyl, methacryl, cyclohexyl, optionally monosubstituted or polysubstituted phenyl, benzyl or phenoxymethyl, with chlorine, bromine, methyl or methoxy as substituents, and furthermore methoxy, ethoxy, isopropoxy, butoxy or isobutoxy, methyl- or ethyl-amino, dimethylamino, phenylamino, chlorophenylamino, chloroethylamino, methoxycarbonylamino, ethoxycarbonylamino or methoxymethylamino; X represents hydrogen or fluorine; Z represents chlorine, bromine, methyl, ethyl, cyclohexyl, methoxy, methylthio, trifluoromethyl, methyoxycarbonyl, cyano, nitro or phenyl, benzyl or phenoxy which is optionally substituted by chlorine; and n represents 0, 1 or 2.

The following compounds of the general formula (I) may be mentioned specifically, in addition to the compounds mentioned later in the preparative examples and in Table 3:

TABLE 1

(I)

| R | X | $Z_n$ |
|---|---|---|
| —CHCl₂ | H | 4-Cl |
| —CH₂Cl | H | 4-Cl |
| —CH₃ | H | 4-⟨phenyl⟩ |
| —NH—⟨phenyl⟩ | H | 4-⟨phenyl⟩ |
| —NH—⟨phenyl⟩—Cl | H | 4-⟨phenyl⟩ |
| —NHCH₃ | H | 4-⟨phenyl⟩ |
| —NHCH₃ | H | 4-Cl; 2-CH₃ |
| —NHCH₃ | H | 2-Cl |
| —NHC₂H₅ | H | 4-⟨phenyl⟩ |
| —C₄H₉-i | H | 4-Br |
| —CH₃ | H | 2,4-Cl₂ |
| —C₂H₅ | H | 2,4-Cl₂ |
| —CH₃ | H | 4-OCH₃ |
| —CH₂Cl | H | 3-CF₃ |
| —CHCl₂ | H | 4-CO—OCH₃ |
| —NHCH₂OCH₃ | H | 4-⟨phenyl⟩ |
| —NHCH₂OC₂H₅ | H | 4-⟨phenyl⟩ |
| —NH—COOCH₃ | H | 4-⟨phenyl⟩ |
| —NH—COOC₂H₅ | H | 4-⟨phenyl⟩ |
| —N(CH₃)₂ | H | 4-⟨phenyl⟩ |
| —OCH₃ | H | 4-⟨phenyl⟩ |
| —CH₃ | H | 4-⟨phenyl⟩—Cl |
| —CH₃ | H | 4-O—⟨phenyl⟩ |
| —CH₃ | H | 4-O—⟨phenyl⟩—Cl |
| —CH₃ | H | 4-CN |

TABLE 1-continued $$\text{(I)} \quad Z_n\text{-}C_6H_4\text{-}O\text{-}CH\text{-}CH(OCOR)\text{-}C(CH_3)(CH_2X)(CH_2F), \text{ with imidazolyl on CH}$$

| R | X | $Z_n$ |
|---|---|-------|
| —CH₃ | H | 4-NO₂ |
| —CH₂OC₂H₅ | H | 2,4-Cl₂ |
| —NHCH(CH₃)₂ | H | 2,4-Cl₂ |
| —NH—CH₂OCH₃ | H | 2,4-Cl₂ |
| —OC₂H₅ | H | 2,4-Cl₂ |
| —C(CH₃)=CH₂ | H | 2,4-Cl₂ |
| —NH—CH₃ | H | 2,4-Cl₂ |
| —CH₂—CH(CH₃)₂ | H | 2,4-Cl₂ |
| —CH₂—C₆H₅ | H | 2,4-Cl₂ |
| —CH₂—CH₂Cl | H | 2,4-Cl₂ |
| —CH₂—CH₂—CH₂Cl | H | 2,4-Cl₂ |
| —NH—C₆H₄—Cl | H | 2,4-Cl₂ |
| —CHCl₂ | H | 2,4-Cl₂ |
| —CH₂Cl | H | 2,4-Cl₂ |
| —C₆H₄—OCH₃ | H | 2,4-Cl₂ |
| —CH₂—O—C₆H₃(Cl)₂ (2,4-Cl₂) | H | 2,4-Cl₂ |
| —H | H | 2,4-Cl₂ |
| —C₆H₅ | H | 2,4-Cl₂ |
| —C₆H₄—Cl | H | 2,4-Cl₂ |
| —CH₂OC₂H₅ | H | 4-Cl |
| —NH—CH(CH₃)₂ | H | 4-Cl |
| —NH—CH₂OCH₃ | H | 4-Cl |
| —OC₂H₅ | H | 4-Cl |
| —CH(CH₃)=CH₂ | H | 4-Cl |
| —CH₂—CH(CH₃)₂ | H | 4-Cl |
| —CH₂—C₆H₅ | H | 4-Cl |
| —CH₂—CH₂Cl | H | 4-Cl |
| —CH₂—CH₂—CH₂Cl | H | 4-Cl |
| —NH—C₆H₄—Cl | H | 4-Cl |
| —C₆H₄—OCH₃ | H | 4-Cl |
| —CH₂—O—C₆H₃(Cl)₂ (2,4-Cl₂) | H | 4-Cl |
| —NH—CH₃ | H | 4-Cl |
| —CH₃ | H | 4-Cl |
| —H | H | 4-Cl |
| —C₆H₅ | H | 4-Cl |
| —C₆H₄—Cl | H | 4-Cl |
| —NHCH₃ | F | 2,4-Cl₂ |
| —NHCH₃ | F | 4-Cl |
| —CH₃ | F | 4-C₆H₄—Cl |
| —NHCH₃ | F | 4-C₆H₅ |
| —NHC₂H₅ | F | 4-C₆H₅ |
| —NHCH₂OCH₃ | F | 4-C₆H₅ |
| —NH—CH(CH₃)₂ | F | 4-C₆H₅ |
| —CH₂OC₂H₅ | F | 4-Cl |
| —NH—CH(CH₃)₂ | F | 4-Cl |
| —NHCH₂OCH₃ | F | 4-Cl |
| —OC₂H₅ | F | 4-Cl |
| —C(CH₃)=CH₂ | F | 4-Cl |
| —CH₂—CH(CH₃)₂ | F | 4-Cl |
| —CH₂—C₆H₅ | F | 4-Cl |
| —CH₂—CH₂Cl | F | 4-Cl |
| —CH₂—CH₂—CH₂Cl | F | 4-Cl |
| —NH—C₆H₄—Cl | F | 4-Cl |
| —CHCl₂ | F | 4-Cl |
| —CH₂Cl | F | 4-Cl |
| —C₆H₄—OCH₃ | F | 4-Cl |
| —CH₂—O—C₆H₃(Cl)₂ (2,4-Cl₂) | F | 4-Cl |

TABLE 1-continued $$(I)$$

Structure: $Z_n$-phenyl-O-CH(N-imidazolyl)-CH(O-CO-R)-C(CH$_3$)(CH$_2$X)-CH$_2$F

| R | X | $Z_n$ |
|---|---|---|
| cyclohexyl | F | 4-Cl |
| phenyl | F | 4-Cl |
| 4-Cl-phenyl | F | 4-Cl |
| —CH$_2$OC$_2$H$_5$ | F | 2,4-Cl$_2$ |
| —NH—CH(CH$_3$)$_2$ | F | 2,4-Cl$_2$ |
| —NH—CH$_2$OCH$_3$ | F | 2,4-Cl$_2$ |
| —OC$_2$H$_5$ | F | 2,4-Cl$_2$ |
| —C(CH$_3$)=CH$_2$ | F | 2,4-Cl$_2$ |
| —CH$_2$—CH(CH$_3$)$_2$ | F | 2,4-Cl$_2$ |
| —CH$_2$-phenyl | F | 2,4-Cl$_2$ |
| —CH$_2$—CH$_2$Cl | F | 2,4-Cl$_2$ |
| —CH$_2$—CH$_2$—CH$_2$Cl | F | 2,4-Cl$_2$ |
| —NH-(4-Cl-phenyl) | F | 2,4-Cl$_2$ |
| —CHCl$_2$ | F | 2,4-Cl$_2$ |
| —CH$_2$Cl | F | 2,4-Cl$_2$ |
| -(4-OCH$_3$-phenyl) | F | 2,4-Cl$_2$ |
| —CH$_2$—O-(2,4-Cl$_2$-phenyl) | F | 2,4-Cl$_2$ |
| cyclohexyl | F | 2,4-Cl$_2$ |
| phenyl | F | 2,4-Cl$_2$ |
| 4-Cl-phenyl | F | 2,4-Cl$_2$ |

If, for example, 1-(4-chlorophenoxy)-1-imidazol-1-yl-3,3-dimethyl-4-fluoro-butan-2-ol and dichloroacetyl chloride are used as starting substances in process variant (a), the course of the reaction can be represented by the following equation:

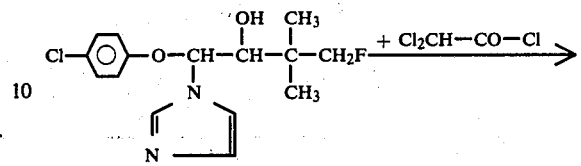

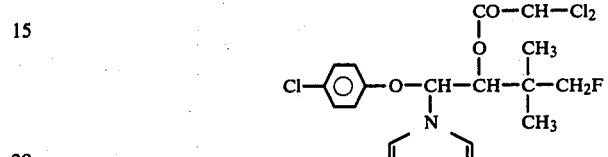

If, for example, 1-(4-chlorophenoxy)-1-imidazol-1-yl-3,3-dimethyl-4-fluoro-butan-2-ol and acetic anhydride are used as starting substances in process variant (b), the course of the reaction can be represented by the following equation:

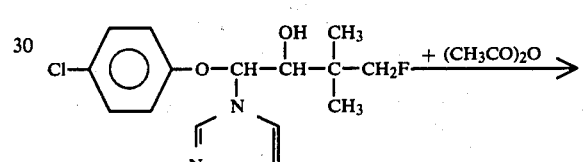

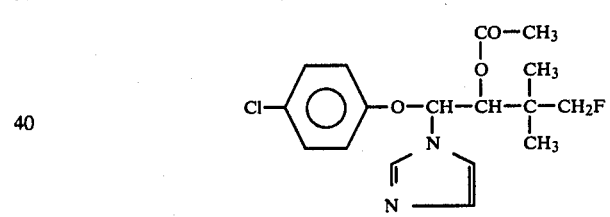

If, for example, 1-(2,4-dichlorophenoxy)-1-imidazol-1-yl-3,3-dimethyl-4-fluoro-butan-2-ol and 4-chlorophenyl isocyanate are used as starting substances in process variant (d), the course of the reaction can be represented by the following equation:

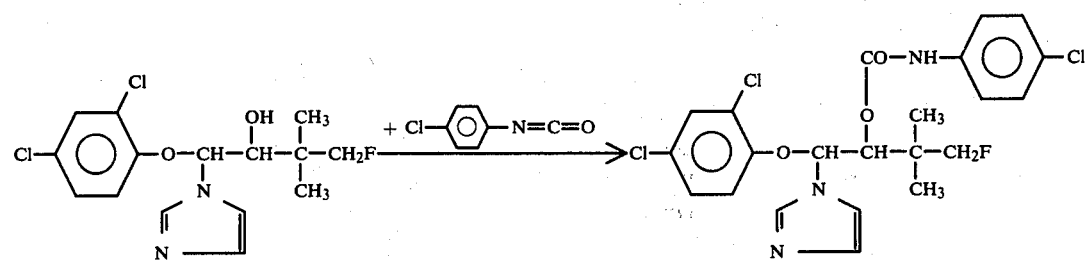

Reactions of 1-imidazolyl-2-hydroxy-butane derivatives of the formula (II) with a ketene of the formula (V) in process variant (c) can be formulated in a corresponding manner.

The formula (II) provides a general definition of the 1-imidazolyl-2-hydroxy-butane derivatives to be used as starting substances for all process variants. In this formula, X, Z and the index n preferably have those meanings which have already been mentioned as preferred in connection with the description of the compounds of the formula (I).

The 1-imidazolyl-2-hydroxy-butane derivatives of the formula (II) have not hitherto been disclosed in the literature; however, they are the subject of U.S. patent application Ser. No. 142,536, filed Apr. 21, 1980, and they can be prepared by reacting halogenoether-ketones of the general formula

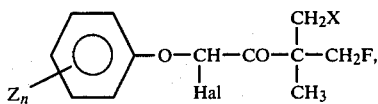
(VII)

in which

X, Z and n have the meanings indicated above and

Hal represents halogen, preferably chlorine or bromine, with imidazole in the presence of an acid-binding agent, for example sodium carbonate or an excess of imidazole, and if appropriate in the presence of an inert organic solvent, for example acetone or acetonitrile, at temperatures between 60° and 120° and reducing the resulting keto derivatives by known methods, for example by reaction with complex hydrides, especially sodium borohydride, if appropriate in the presence of a polar organic solvent, for example alcohols, at temperatures between 0° and 30° C., or by reaction with aluminum isopropylate in the presence of an inert organic solvent, for example isopropanol, at temperatures between 20° and 120° C. Working up is effected in the customary manner.

The halogenoether-ketones of the formula (VII) have not been hitherto disclosed in the literature. However, they are also the subject of U.S. patent application Ser. No. 142,536, filed Apr. 21, 1980, supra. They can, however, be obtained by known processes (see, for example, German Published Specification DOS No. 2,632,602) for example by reacting known phenols of the general formula

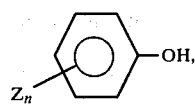
(VIII)

in which Z and n have the meanings indicated above, with a halogeno-ketone of the general formula

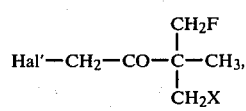
(IX)

in which

X has the meaning indicated above and

Hal' represents chlorine or bromine.

The active hydrogen atom which still remains is then replaced by halogen in the customary manner (see also the preparative examples).

The halogeno-ketones of the formula (IX) have also hitherto not been disclosed in the literature, and are also the subject of the above-mentioned earlier application. However, they can be obtained in a generally custom-ary and known manner, by adding chlorine or bromine to fluorine derivatives of 3,3-dimethyl-butan-2-one of the general formula

(X)

in which X has the meaning indicated above, in the presence of an inert organic solvent, for example ether or a chlorinated hydrocarbon, at room temperature (see also the preparative examples), or by reacting the fluorine derivatives with customary chlorinating agents, for example sulphuryl chloride, at 20° to 60° C.

The fluorine derivatives of 3,3-dimethyl-butan-2-one, of the formula (X), have also not hitherto been disclosed in the literature. However, they are the subject of U.S. Patent Application Ser. No. 77,447, filed Sept. 20, 1979. The fluorine derivatives of 3,3-dimethyl-butan-2-one, of the formula (X), are obtained when sulphonic acid esters of the general formula

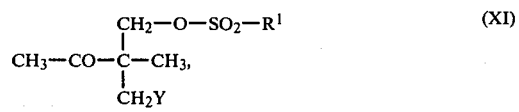
(XI)

in which $R^1$ represents alkyl with 1 to 4 carbon atoms, in particular methyl, or aryl with 6 to 12 carbon atoms, in particular phenyl or tolyl, and Y represents hydrogen or the group $-O-SO_2-R^1$, are reacted with a metal fluoride, for example sodium fluoride or potassium fluoride, in the presence of a polar organic solvent, for example di-, tri- or tetraethylene glycol, at temperatures between 80° and 250° C. (see also the preparative examples).

Sulphonic acid esters of the formula (XI) are disclosed in J. Org. Chem. 35, 2391 (1970) and can be prepared from the corresponding hydroxy-butanones and sulphochlorides in the presence of bases, by processes which are known from the literature (see, for example, Houben-Weyl, Methoden der Org. Chemie (Methods of Organic Chemistry), Volume IX, pages 388 and 663, and the statements in the preparative examples).

Specific examples of the starting substances of the formula (II) which may be mentioned are:

TABLE 2

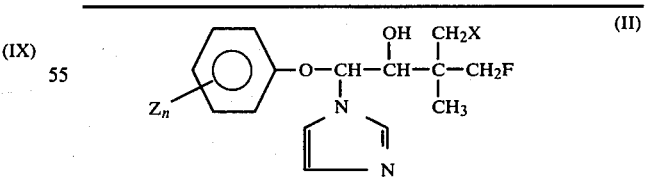
(II)

| $Z_n$ | X | $Z_n$ | X |
|---|---|---|---|
| — | H | — | F |
| 2-Cl | H | 2-Cl | F |
| 3-Cl | H | 3-Cl | F |
| 4-Cl | H | 4-Cl | F |
| 2-F | H | 2-F | F |
| 3-F | H | 3-F | F |
| 4-F | H | 4-F | F |
| 2-Br | H | 2-Br | F |
| 3-Br | H | 3-Br | F |

TABLE 2-continued $$\text{(II)} \quad \underset{Z_n}{\underset{|}{\bigcirc}}-O-CH-CH-\underset{|}{\overset{|}{C}}-CH_2F$$
with OH, CH₂X substituents, N-pyrrole ring, and CH₃

| $Z_n$ | X | $Z_n$ | X |
|---|---|---|---|
| 4-Br | H | 4-Br | F |
| 2,4-Cl₂ | H | 2,4-Cl₂ | F |
| 2-CH₃ | H | 2-CH₃ | F |
| 4-CH₃ | H | 4-CH₃ | F |
| 2-Cl, 4-CH₃ | H | 2-Cl, 4-CH₃ | F |
| 4-Cl, 2-CH₃ | H | 4-Cl, 2-CH₃ | F |
| 4-I | H | 4-I | F |
| 4-CN | H | 4-CN | F |
| 2-NO₂ | H | 2-NO₂ | F |
| 4-COOCH₃ | H | 4-COOCH₃ | F |
| 4-COOC₂H₅ | H | 4-COOC₂H₅ | F |
| 4-C₆H₅ | H | 4-C₆H₅ | F |
| 2-C₆H₅ | H | 2-C₆H₅ | F |
| 4-(4-Cl-C₆H₄) | H | 4-(4-Cl-C₆H₄) | F |

The formula (III) provides a general definition of the acid halides also to be used as starting substances for process variant (a). In this formula, R preferably represents those radicals which have already been mentioned as preferred in connection with the description of the compounds of the formula (I).

Acid halides of the formula (III) are known, and they can be prepared by customary processes, for example by reaction of carboxylic acids or alkali metal salts thereof with acid halides of phosphorus or sulphur. These methods are known from general textbooks of organic chemistry.

The formula (IV) provides a general definition of the acid anhydrides also to be used as starting substances for process variant (b). In this formula, P preferably represents those radicals which have already been mentioned as preferred in connection with the description of the compounds of the formula (I).

Acid anhydrides of the formula (IV) are known, and they can be prepared by known processes, for example by the action of acid chlorides on the alkali metal salts of carboxylic acids. These processes are generally known.

The formula (V) provides a general definition of the ketenes also to be used as starting substances for process variant (c). In this formula, R' and R" are identical or different and preferably each represent hydrogen, alkyl with 1 to 7, in particular 1 to 5, carbon atoms, alkenyl with up to 3 carbon atoms or halogenomethyl with 1 to 3 halogen atoms, in particular fluorine or chlorine. R' and R" also preferably represent halogen, such as, in particular, chlorine and bromine, alkoxy with 1 to 3 carbon atoms or optionally monosubstituted or polysubstituted phenyl, preferred substituents being halogen, cyano, nitro or alkyl with 1 to 2 carbon atoms.

Ketenes of the formula (V) are known and they can be prepared by known processes, for example by thermolysis of ketones or by dehydration of carboxylic acids (see Houben-Weyl, "Methoden der organischen Chemie" ("Methods of Organic Chemistry"), Volume 7/4, Georg Thieme Verlag).

The formula (VI) provides a general definition of the isocyanates also to be used as starting substances for process variant (d). In this formula, R'" preferably represents straight-chain or branched alkyl with 1 to 12 carbon atoms, halogenoalkyl with up to 4 carbon atoms and up to 5 identical or different halogen atoms, such as, in particular, fluorine and chlorine atoms, and alkoxycarbonyl and alkoxyalkyl with in each case 1 to 4 carbon atoms in each alkyl part. R'" also preferably represents optionally monosubstituted or polysubstituted phenyl, preferred substituents being halogen, nitro, cyano, straight-chain or branched alkyl with 1 to 4 carbon atoms, alkoxy and alkylthio with in each case 1 or 2 carbon atoms, halogenoalkyl with up to 2 carbon atoms and up to 5 identical or different halogen atoms, such as, in particular, fluorine and chlorine atoms, and alkoxycarbonylalkenyl with 1 to 4 carbon atoms in the alkyl part and 2 to 4 carbon atoms in the alkenyl part.

Isocyanates of the formula (VI) are known and they can be prepared by generally customary and known processes, for example by reaction of amines with phosgene and subsequent heating of the product.

Preferred solvents for the reaction according to process variant (a) are any of the inert organic solvents. These include, as preferences, nitriles, such as propionitrile, and in particular acetonitrile; ethers, such as tetrahydrofuran or dioxane; esters, such as ethyl acetate; aromatic hydrocarbons, such as benzene or toluene; and halogenated hydrocarbons, such as methylene chloride, carbon tetrachloride or chloroform. For simplicity, the acid chloride employed can also be used as the solvent, whereupon an appropriate excess becomes necessary.

The reaction temperatures can be varied within a substantial range in carrying out process variant (a). In general, the reaction is carried out between 0° and 100° C., preferably between 20° and 85° C. If a solvent is present, the reaction is optionally carried out at the boiling point of the particular solvent.

If appropriate, process variant (a) can be carried out in the presence of an acid-binding agent (hydrogen halide acceptor); any of the customary acid-binding agents can be used here. These include organic bases, preferably tertiary amines, for example triethylamine; and furthermore inorganic bases, for example alkali metal hydroxides and alkali metal carbonates.

Equimolar amounts of the reactants are preferably used in carrying out process variant (a). The resultant compound of the formula (I) is obtained in the form of its hydrohalide and can be isolated as such by precipitation by adding an organic solvent, for example hexane, and filtration, and if appropriate purification by recrystallization. The compound of the formula (I) can also be isolated in the form of its free base by adding aqueous sodium bicarbonate solution to the reaction mixture and isolating the base by customary methods.

Preferred diluents for the reaction according to process variant (b) are any of the inert organic solvents. These include, as preferences, the solvents listed for process variant (a) and the particular acid anhydrides of the formula (IV) used.

Catalysts which can be used in process variant (b) are preferably any of the customary acid and basic catalysts, for example sulphuric acid, hydrogen chloride, hydrogen bromide, boron trifluoride, zinc chloride, sodium acetate, sodium benzoate, sodium carbonate, calcium oxide and magnesium oxide.

The reaction temperatures can be varied within a substantial range in carrying out process variant (b). In general, the reaction is carried out between 0° and 150° C., preferably between 80° and 120° C.

Equimolar amounts of the reactants are preferably used in carrying out process variant (b). For simplicity, the acid anhydride of the formula (IV) employed can also be used as the solvent, whereupon an appropriate excess becomes necessary. Isolation of the compounds of the formula (I) is effected in the customary manner.

Preferred diluents for the reaction according to process variant (c) are any of the inert organic solvents. These include, as preferences, the solvents listed for process variant (a).

Catalysts which can be used in process variant (c) are preferably any of the customary acid and basic catalyst. These include, as preferences, the substances listed for process variant (b).

The reaction temperatures can be varied within a certain range in carrying out process variant (c). In general, the reaction is carried out between −10° and 70° C., preferably between 0° and 40° C.

Equimolar amounts of the reactants are preferably used in carrying out process variant (c). Isolation of the compounds of the formula (I) is effected by customary methods.

Preferred diluents for the reaction according to process variant (d) are any of the inert organic solvents. These include, as preferences, the solvents listed for process variant (a).

Catalysts which can preferably be used in process variant (d) are tertiary bases, such as triethylamine and pyridine, or organo-tin compounds, such as dibutyltin dilaurate.

The reaction temperatures can be varied within a substantial range in carrying out process variant (d). In general, the reaction is carried out between 0° and 100° C., preferably between 20° and 40° C.

Equimolar amounts of the reactants are preferably used in carrying out process variant (d). To isolate the compounds of the formula (I), the solvent is distilled off and the residue is worked up by customary methods.

The following acids can be used for the preparation of physiologically acceptable acid addition salts of the compounds of the formula (I): hydrogen halide acids (for example hydrobromic acid and, in particular, hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicylic acid, sorbic acid and lactic acid) and sulphonic acids (for example p-toluenesulphonic acid and 1,5-naphthalenedisulphonic acid).

The acid addition salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Preferred anions of the salts are those which are derived from the following acids: hydrogen halide acids (for example hydrochloric acid and hydrobromic acid), phosphoric acid, nitric acid and sulphuric acid.

The metal salt complexes of the compounds of the formula (I) can be obtained in a simple manner by customary processes, for example by dissolving the metal salt in alcohol, for example ethanol, and adding the solution to the compound of the formula (I). The metal salt complexes can be purified in a known manner, for example by filtration, isolation and, if appropriate, by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Comycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating those fungi which cause powdery mildew diseases; thus they can be used for combating Podosphaera species, for example the powdery mildew of apple causative organism (*Podosphaera leucotricha*) or Erysiphe species, for example the powdery mildew of cucumber causative organism (*Erysiphe cichoracearum*) or the powdery mildew of cereal causative organism (*Erysiphe graminis*), and for combating other cereal diseases, such as cereal rust.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to any liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellants, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, immersion, spraying, atomising, misting, vaporising, injecting, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g, preferably 0.01 to 10 g, are generally employed per kilogram of seed.

For the treatment of soil, active compound concentrations of 0.00001 to 0.1% by weight, preferably 0.0001 to 0.02%, are generally employed at the place of action.

When applied in certain amounts, the substances according to the invention also exhibit a growth regulating action.

The present invention also provides a fungicidal composition containing as active ingredient a compound of the present invention in admixture with a solid or liquefied gaseous diluent or carrier or in admixture with a liquid diluent or carrier containing a surface-active agent.

The present invention also provides a method of combating fungi which comprises applying to the fungi, or to a habitat thereof, a compound of the present invention alone or in the form of a composition containing as active ingredient a compound of the present invention in admixture with a diluent or carrier.

The present invention further provides crops protected from damage by fungi by being grown in areas in which immediately prior to and/or during the time of the growing a compound of the present invention was applied alone or in admixture with a diluent or carrier.

It will be seen that the usual methods of providing a harvested crop may be improved by the present invention.

PREPARATIVE EXAMPLES

Example 1

(a)

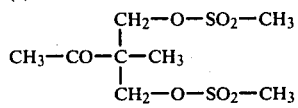

66 g (0.5 mol) of 3-oxo-2,2-bis-(hydroxymethyl)butane (for the preparation, see Beilstein H 1, E III 3306, IV 4132 and J. Chem. Soc., London, 1932, 2671) were dissolved in 300 ml of 1,2-dichlorethane, 114.5 g (1 mol) of methanesulphonyl chloride were added dropwise, and 158 g (2 mol) of pyridine were added dropwise at 0°–5° C. The mixture was subsequently stirred at room temperature for 15 hours and then poured onto 600 ml of ice-water and 100 ml of concentrated hydrochloric acid. A solid thereby precipitated and was filtered off. The aqueous phase was extracted with 1,000 ml of methylene chloride; the solid was dissolved in the methylene chloride phase, the organic phase was dried over sodium sulphate, the solvent was distilled off under a waterpump vacuum and the residue was suspended in 200 ml of ether. The residue was filtered off and washed with 100 ml of ether. 100 g (about 70% of theory) of 2-acetyl-2-methyl-propane-1,3-diol bismethanesulphonate of melting point 105°–108° C. were obtained.

(b)

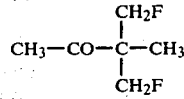

400 ml of tetraethylene glycol and 46.4 g (0.8 mol) of potassium fluoride were initially introduced into a three-necked flask with a stirrer, dropping funnel and Liebig condenser with a cooled receiver, and the mixture was heated to 170° C. A waterpump vacuum (pressure: about 20 to 30 mbars) was applied to the adaptor of the Liebig condenser. 57.6 g (0.2 mol) of 2-acetyl-2-methyl-propane-1,3-diol bismethanesulphonate, dissolved in 100 ml of tetraethylene glycol, were then added dropwise in the course of 45 minutes. The 3,3-bisfluoromethyl-butan-2-one formed was distilled off into the cooled receiver during the reaction. After the dropwise addition, distillation was continued for a further hour at 175° C.

The distillate collected was then redistilled. 14 g (about 51.5% of theory) of 3,3-bisfluoromethyl-butan-2-one of boiling point 43°–46° C./12 mm Hg were obtained.

(c)

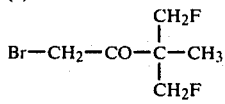

903 g of the bromine were slowly added dropwise to a mixture of 757 g (5.58 mol) of 3,3-bisfluoromethyl-2-butanone and 4.5 liters of methylene chloride at 20° to 30° C., while cooling and stirring. The yellowish solution was subsequently stirred for a further hour at 20° C. After distilling off the solvent, the residue was distilled in vacuo. 1,030 g (86% of theory) of 3,3-bisfluoromethyl-1-bromo-butan-2-one of boiling point 49°–53° C./0.15 mm Hg were obtained.

(d)

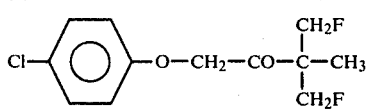

171.2 g (0.79 mol) of 3,3-bisfluoromethyl-1-bromo-butan-2-one were added dropwise to a stirred mixture of 102 g (0.79 mol) of p-chlorophenol and 110 g (0.79 mol) of powdered potassium carbonate in 500 ml of acetone at 20° to 30° C. The mixture was subsequently stirred at 40° C. for 4 hours, the inorganic salt was filtered off and the filtrate was concentrated. The residue was distilled under a high vacuum. 190.5 g (90% of theory) of 3,3-bisfluoromethyl-1-(4-chlorophenoxy)-butan-2-one of boiling point 113°–117° C./0.1 mm Hg were obtained.

(e)

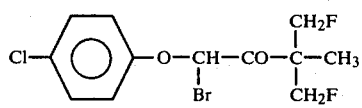

166 g (0.632 mol) of 3,3-bisfluoromethyl-1-(4-chlorophenoxy)-butan-2-one were dissolved in 500 ml of methylene chloride, and 100 g (0.625 mol) of bromine were added dropwise at 20° to 30° C., while stirring and cooling. The mixture was subsequently stirred at 20° C. for 2 hours. After distilling off the solvent in vacuo, the residue was crystallized from petroleum ether. 190 g (88% of theory) of 3,3-bisfluoromethyl-1-bromo-1-(4-chlorophenoxy)-butan-2-one of melting point 54°–55° C. were obtained.

(f)

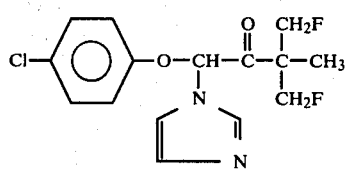

61.5 g (0.18 mol) of 3,3-bisfluoromethyl-1-bromo-(4-chlorophenoxy)-butan-2-one were stirred with 27.2 g (0.4 mol) of imidazole in 500 ml of acetonitrile at 45° C. for 4 hours. The solvent was distilled off under a water-pump vacuum, the oil which remained was taken up in 500 ml of methylene chloride, the organic phase was washed twice with 1,000 ml of water and dried over sodium sulphate and the solvent was distilled off. The oil was taken up in acetone, 36 g (0.1 mol) of 1,5-naphthalene-disulphonic acid tetrahydrate were added and the precipitate formed was filtered off. The precipitate was treated with sodium bicarbonate solution.

14 g (24% of theory) of 3,3-bisfluoromethyl-1-(4-chlorophenoxy)-1-(imidazol-1-yl)-butan-2-one were obtained as a viscous oil which was further reacted directly.

(g)

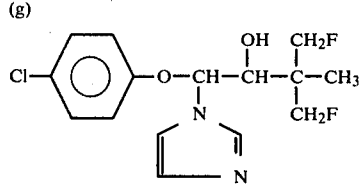

31.9 g (0.097 mol) of 3,3-bisfluoromethyl-1-(4-chlorophenoxy)-1-(imidazol-1-yl)-butan-2-one were dissolved in 600 ml of methanol, and 5.45 g (0.14 mol) of sodium borohydride were added in portions at 0° to 5° C. The mixture was subsequently stirred for 15 hours, 15 ml of concentrated hydrochloric acid were added and the mixture was stirred at room temperature for 2 hours. Thereafter, the reaction mixture was stirred into 800 ml of aqueous, saturated sodium bicarbonate solution. It was extracted with 1,000 ml of methylene chloride and the organic phase was washed twice with 1,000 ml of water each time, dried over sodium sulphate and concentrated by distilling off the solvent in vacuo. The oil which remained was stirred with isopropyl ether. 22.2 g (67.5% of theory) of 3,3-bisfluoromethyl-1-(4-chlorophenoxy)-1-(imidazol-1-yl)-butan-2-ol of melting point 137° were obtained.

(h)   (1)

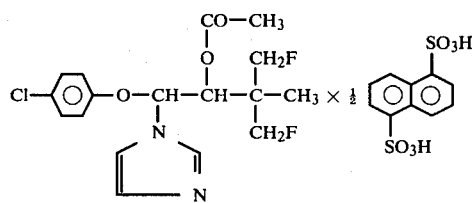

Process variant (b)

12.2 g (0.037 mol) of 3,3-bisfluoromethyl-1-(4-chlorophenoxy)-1-(imidazol-1-yl)-butan-2-ol were dissolved in 70 ml of acetic anhydride. The solution was stirred at 100° C. for 16 hours, the excess acetic anhydride was distilled off in vacuo and the residue was taken up in 300 ml of methylene chloride. The organic phase was washed twice with 800 ml of water each time, dried over sodium sulphate and concentrated. The residue was taken up in 100 ml of acetone, and a solution of 9 g (0.038 mol) of 1,5-naphthalenedisulphonic acid in 50 ml of acetone was added. After 2 hours, the precipitate which had formed was filtered off and dried. 13 g (68% of theory) of 2-acetoxy-3,3-bisfluoromethyl-1-(4-chlorophenoxy)-1-(imidazol-1-yl)-butane 1,5-naphthalenedisulphonate of melting point 221°–224° C. were obtained.

EXAMPLE 2

(a)

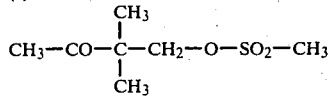

232 g (2 mols) of 3,3-dimethyl-4-hydroxy-2-butanone (for the preparation, see Peilstein H 1 E III 3239, IV 4030 and Bull. Soc. Chim. France 1964, 2849) in 700 ml of absolute pyridine were reacted with 229 g (2 mol) of methanesulphonyl chloride at 0° to 5° C. After leaving the mixture to stand at 20° C. for 12 hours, it was diluted with methylene chloride and extracted by shaking with ice-water. The organic phase was dried and freed from solvent in vacuo and the residue was fractionated over a column. 332 g (86% of theory) of 2,2-dimethyl-3-oxobutyl methanesulphonate of boiling point 106°–120° C./0.12 mm Hg were obtained.

(b)

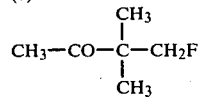

38.8 g (0.2 mol) of 2,2-dimethyl-3-oxobutyl methanesulphonate were added dropwise to a suspension, in a three-necked stirred flask with a descending condenser, of 23.2 g (0.4 mol) of dry potassium fluoride in 400 ml of distilled tetraethylene glycol at 160° C. and under 20 mbars in the course of 2 hours and the mixture was subsequently stirred for a further 2 hours. The reaction product which had distilled out was condensed in a descending condenser and collected in a subsequent low temperature trap. 20.9 g (89% of theory) of 3,3-dimethyl-4-fluoro-2-butanone of boiling point 130°–134° C. were obtained.

(c)

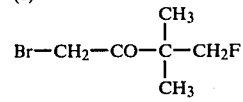

480 g of bromine were slowly added dropwise to a mixture of 354 g (3 mols) of 3,3-dimethyl-4-fluoro-2-butanone and 2,000 ml of ether at 20° to 30° C., while cooling and stirring. The yellowish solution was subsequently stirred for a further hour at 20° C. and 500 ml of water were then carefully added. The ether phase was separated off, washed several times with water and dried over sodium sulphate. After distilling off the solvent, the residue was distilled under a waterpump vacuum. 472 g (80% of theory) of 1-bromo-3,3-dimethyl-4-fluoro-2-butanone of boiling point 80°–90° C./11 mm Hg were obtained.

(d)

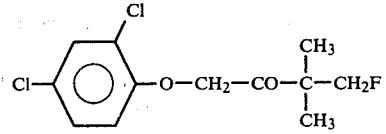

157 g (0.79 mol) of 1-bromo-3,3-dimethyl-4-fluoro-2-butanone were added dropwise to a stirred mixture of 129 g (0.79 mol) of 2,4-dichlorophenol and 110 g (0.79 mol) of powdered potassium carbonate in 500 ml of acetone at 20° to 30° C., while cooling. The mixture was subsequently stirred at 20° C. for 2 hours, the inorganic salt was filtered off and the filtrate was concentrated. 199.3 g (90% of theory) of 1-(2,4-dichlorophenoxy)-3,3-dimethyl-4-fluoro-2-butanone were obtained as an oil, which was further reacted directly.

(e)

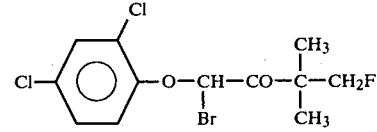

199.5 g (0.71 mol) of 1-(2,4-dichlorophenoxy)-3,3-dimethyl-4-fluoro-2-butanone were dissolved in 500 ml of chloroform and 114 g (0.71 mol) of bromine were added dropwise at 20° to 30° C., while stirring and cooling. The mixture was subsequently stirred at 20° C. for 2 hours, 200 ml of water were carefully added to the chloroform phase was washed several times with ice-water and dried over sodium sulphate. After distilling off the solvent in vacuo, 205.2 g (78% of theory) of 1-bromo-1-(2,4-dichlorophenoxy)-3,3-dimethyl-4-fluoro-2-butanone were obtained as an oil which was further reacted directly.

(f)

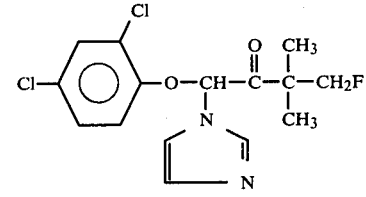

157.5 g (0.44 mol) of 1-bromo-1-(2,4-dichlorophenoxy)-3,3-dimethyl-4-fluoro-2-butanone were dissolved in 500 ml of acetonitrile and the solution was added dropwise to a solution of 109 g (1.6 mol) of imidazole in 600 ml of acetonitrile. The mixture was heated under reflux for 10 hours. Thereafter, the solvent was distilled off under a waterpump vacuum, the residue was taken up in 1,000 ml of methylene chloride and the methylene chloride mixture was washed three times with 500 ml of water each time. The organic phase was dried over sodium sulphate and filtered and the filtrate was concentrated under a waterpump vacuum by distilling off the solvent. The residue was dissolved in 500 ml of ethanol, 40 ml of concentrated hydrochloric acid were added and the solvent was distilled off under a waterpump vacuum. The residue was stirred with 50 ml of ether, whereupon it crystallized. 66 g (39.3% of theory) of 1-(2,4-dichlorophenoxy)-3,3-dimethyl-4-fluoro-1-(imidazol-1-yl)-2-butanone hydrochloride of melting point 91°–110° C. were obtained.

(g)

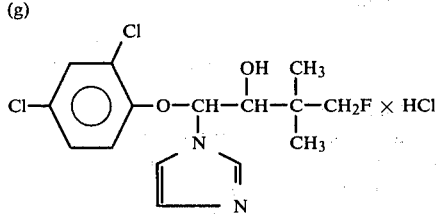 × HCl 44 g (0.1275 mol) of 1-(2,4-dichlorophenoxy)-3,3-dimethyl-4-fluoro-1-(imidazol-1-yl)-2-butanone were dissolved in 300 ml of methanol, and 6.3 g of sodium borohydride were added at 0° to 5° C. The mixture was subsequently stirred at room temperature for 15 hours, 60 ml of concentrated hydrochloric acid were added dropwise, while cooling with ice, the mixture was stirred at room temperature for 10 hours and the solvent was distilled off under a waterpump vacuum. The residue was taken up in 250 ml of methylene chloride, the methylene chloride mixture was stirred in 500 ml of aqueous, saturated sodium bicarbonate solution, the methylene chloride phase was separated off and washed three times with 100 ml of water each time, the organic phase was dried over sodium sulphate and the solvent was distilled off. The oil which remained was taken up in 200 ml of ether, 50 ml of ethereal hydrochloric acid were added and the solvent was distilled off. 28.2 g (58% of theory) of 1-(2,4-dichlorophenoxy)-3,3-dimethyl-4-fluoro-1-(imidazol-1-yl)-2-butanol hydrochloride of melting point 184°–210° C. were obtained.

(h)

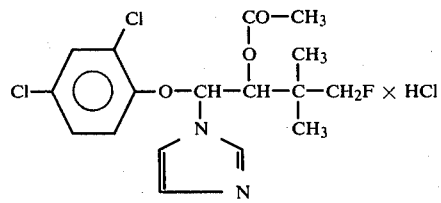 × HCl  (2)

Process variant (b)

17.3 g (0.05 mol) of 1-(2,4-dichlorophenoxy)-3,3-dimethyl-4-fluoro-1-(imidazol-1-yl)-butan-2-ol were dissolved in 100 ml of acetic anhydride and, after adding 0.1 g of sodium acetate, the mixture was stirred at 100° C. for 10 hours. Thereafter, the reaction solution was allowed to cooled to room temperature, stirred into 500 ml of water and left to stand for 15 hours. The aqueous phase was extracted twice with 200 ml of methylene chloride each time. The combined organic phases were washed with 100 ml each of sodium bicarbonate solution and water, dried over sodium sulphate and concentrated in vacuo. The residue was taken up in 100 ml of ether, 20 ml of ethereal hydrochloric acid were added, the solvent was distilled off in vacuo and the residue was stirred with 50 ml of ether. 15.3 g (72% of theory) of 2-acetoxy-1-(2,4-dichlorophenoxy)-3,3-dimethyl-4-fluoro-1-(imidazol-1-yl)-butane hydrochloride of melting point of 198°–200° C. were obtained.

The following compounds of the general formula

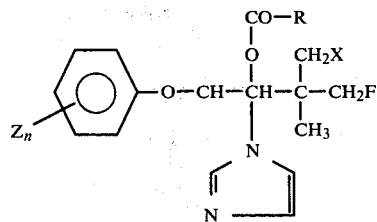 (I)

were obtained in a corresponding manner and according to process variants (a) to (d):

| Compound No. | $Z_n$ | R | X | Melting point (°C.) |
|---|---|---|---|---|
| 3 | 4-F | —CH₃ | F | 200–210 (× ½ NDS) |
| 4 | 2,4-Cl₂ | —CH₃ | F | 195–205 (× ½ NDS) |
| 5 | 4-(C₆H₃Cl)- | —CH₃ | F | 256 (× ½ NDS) |
| 6 | 2,4-Cl₂ | —NH—C₆H₄—Cl | F | 142–44 |
| 7 | 4-Cl | —NH—C₆H₄—Cl | F | 146–48 |
| 8 | 4-C₆H₅ | —NH—C₆H₄—Cl | F | 124 |
| 9 | 2,4-Cl₂ | —C₆H₅ | F | 140–42 |
| 10 | 4-Cl | —C₆H₅ | F | 58–60 |
| 11 | 4-Cl | —CH₂CH₂CH₂Cl | F | 225–28 (× ½ NDS) |
| 12 | 4-Cl | —C₆H₄—Cl | F | >260 (× ½ NDS) |
| 13 | 2,4-Cl | —C₆H₄—Cl | F | >260 (× ½ NDS) |
| 14 | 2,4-Cl₂ | —CH₂CH₂CH₂Cl | F | 255-60 (× ½ NDS) |
| 15 | 2,4-Cl | CHCl₂ | F | 215–225 (× ½ NDS) |
| 16 | 2,4-Cl₂ | NHCH₃ | F | 250 (× ½ NDS) |
| 17 | 4-Cl | NHCH₃ | F | 121–27 |
| 18 | 4-Cl | CH₂—OC₂H₅ | F | 225–27 (× ½ NDS) |
| 19 | 2,4-Cl | CH₂OC₂H₅ | F | 222–4 (× ½ NDS) |

NOTE: NDS = 1,5-naphthalenedisulphonate.

The fungicidal activity of the compounds of this invention is illustrated by the following examples wherein the compounds according to the present invention are each identified by the number (given in brackets) from the preparative examples hereinabove.

The known comparison compounds are identified as follows:

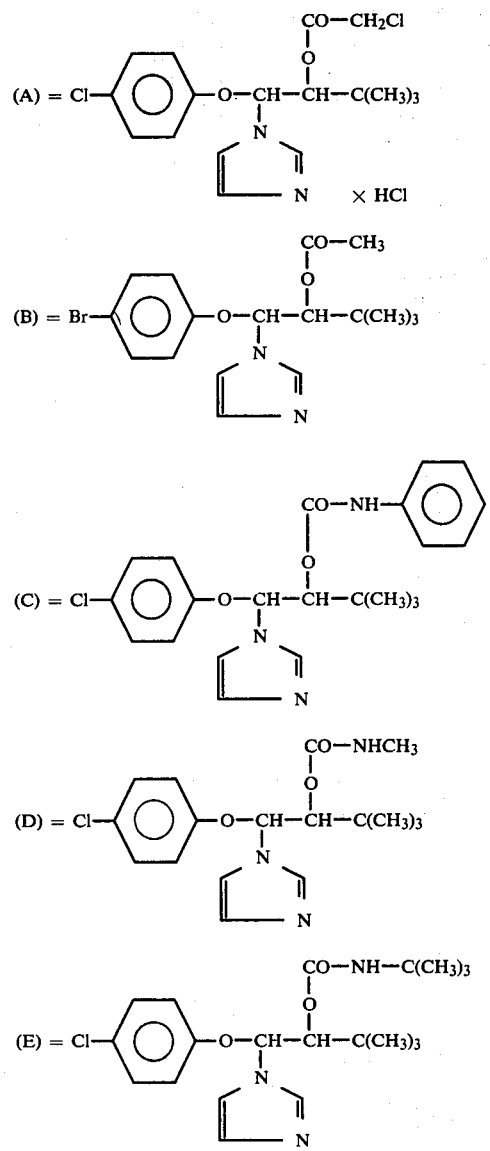

EXAMPLE 3

Shoot treatment test/powdery mildew of cereals (leaf-destructive mycosis)/protective To produce a suitable preparation of active compound, 0.25 part by weight of active compound was taken up in 25 parts by weight of dimethylformamide and 0.06 part by weight of alkylaryl polyglycol ether; 975 parts by weight of water were then added. The concentrate was diluted with water to the desired final concentration of the spray liquor.

To test for protective activity, single-leaved young barley plants of the Amsel variety were sprayed with the preparation of active compound until dew-moist. After drying, the barley plants were dusted with spores of *Erysiphe graminis* var. hordei.

After 6 days' dwell time of the plants at a temperature of 21–22 deg.C. and 80–90% atmospheric humidity the occurrence of mildew pustules on the plants was evaluated. The degree of infection was expressed as a percentage of the infection of the untreated control plants. 0% denoted no infection and 100% denoted the same degree of infection as in the case of the untreated control. The more active the compound, the lower was the degree of mildew infection.

In this test, for example, the following compound exhibited a very good action which was superior to that of the compound (A) known from the prior art: compound (1).

EXAMPLE 4

Shoot treatment test/cereal rust (leaf-destructive mycosis)/protective

To produce a suitable preparation of active compound, 0.25 part by weight of active compound was taken up in 25 parts by weight of dimethylformamide and 0.06 parts by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20 deg.C. and 100% relative atmospheric humidity.

After 10 days' dwell time of the plants at a temperature of 20 deg.C. and 80–90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The more active the compound, the lower was the degree of rust infection.

In this test, for example, the following compound exhibited a very good action which was superior to that of the compound (B) known from the prior art: compound (2).

EXAMPLE 5

Erysiphe test (cucumber)/protective

Solvent: 4.7 parts by weight of acetone
Emulsifier: 0.3 part by weight of alkylaryl polyglycol ether
Water: 95 parts by weight The amount of the active compound required for the desired concentration of active compound in the spray liquid was mixed with the stated amount of solvent and the concentrate was diluted with the stated amount of water containing the stated amount of emulsifier.

Young cucumber plants with about three foliage leaves were sprayed with the spray liquid until dripping wet. The cucumber plants remained in a greenhouse for 24 hours to dry. They were then, for the purpose of inoculation, dusted with conidia of the fungus *Erysiphe cichoracearum*. The plants were subsequently placed in a greenhouse at 23–24 degrees C. and at a relative atmospheric humidity of about 75%.

After 12 days, the infection of the cucumber plants was determined. The assessment data were converted to percent infection. 0% meant no infection; 100% meant that the plants were totally infected.

In this test, for example, the following compounds exhibited a very good action which was superior to that of compounds (A) and (C) known from the prior art: compounds (1) and (2).

EXAMPLE 6

Podosphaera test (apple)/protective
Solvent: 4.7 parts by weight of acetone
Emulsifier: 0.3 part by weight of alkylaryl polyglycol ether
Water: 95 parts by weight The amount of active compound required for the desired concentration of the active compound in the spray liquid was mixed with the stated amount of solvent, and the concentrate was diluted with the stated amount of water which contained the stated amount of emulsifier.

Young apple seedlings in the 4–6 leaf stage were sprayed with the spray liquid until dripping-wet. The plants remained in a greenhouse for 24 hours at 20 deg.C. and at a relative atmospheric humidity of 70%. They were then inoculated by dusting the conidia of the apple powdery mildew causative organism (*Podosphaera leucotricha*) and placed in a greenhouse at a temperature of 21 23 degrees C. and at a relative atmospheric humidity of about 70%.

10 days after the inoculation, the infection of the seedlings was determined. The assessment data were converted to % infection. 0% meant no infection; 100% meant that the plants were completely infected.

In this test, for example, the following compounds exhibited a very good action which was superior to that of the compounds (C) and (D) known from the prior art: compounds (1) and (2).

EXAMPLE 7

Mycelium growth test
Nutrient medium used:
  20 parts by weight of agar-agar
  200 parts by weight of potato decoction
  5 parts by weight of malt
  15 parts by weight of dextrose
  5 parts by weight of peptone
  2 parts by weight of disodium hydrogen phosphate
  0.3 part by weight of calcium nitrate
Composition of the solvent mixture:
  0.19 part by weight of acetone or dimethylformamide
  0.01 part by weight of emulsifier (alkylaryl polyglycol ether)
  1.80 parts by weight of water
Ratio of solvent mixture to nutrient medium:
  2 parts by weight of solvent mixture
  100 parts by weight of agar nutrient medium The amount of active compound required for the desired active compound concentration in the nutrient medium was mixed with the stated amount of solvent mixture. The concentrate was thoroughly mixed, in the stated proportion, with the liquid nutrient medium (which had been cooled to 42 deg.C) and was then poured into Petri dishes of 9 cm diameter. Control plates to which the preparation had not been added were also set up.

When the nutrient medium had cooled and solidified, the plates were inoculated with the species of organisms stated hereinbelow and incubated at about 21 degrees C.

Evaluation was carried out after 4–10 days, dependent upon the speed of growth of the organisms. When evaluation was carried out the radial growth of the organism on the treated nutrient media was compared with the growth on the control nutrient medium.

In this test for example, the following compound exhibited a very good action which was superior to that of the compounds (D) and (E) known from the prior art: compound (2).

It will be understood that the specification and examples are illustrative but not limitative of the present invention and that other embodiments within the spirit and scope of the invention will suggest themselves to those skilled in the art.

We claim:

1. A compound of the formula

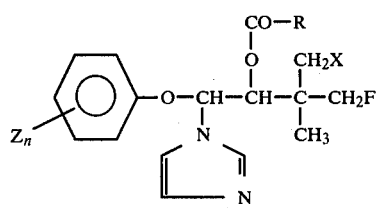

in which
R represents straight-chain or branched alkyl with 1 to 8 carbon atoms, straight-chain or branched alkenyl or alkynyl with in either case 2 to 4 carbon atoms, halogenoalkyl with 1 to 2 carbon atoms and 1 to 5 halogen atoms, alkoxy with 1 to 4 carbon atoms, alkoxyalkyl with 1 to 4 carbon atoms in each alkyl part, cycloalkyl with 5 to 7 carbon atoms, optionally substituted phenyl or phenylalkyl or phenoxyalkyl which are optionally substituted in the phenyl part and have in each case up to 2 carbon atoms in the alkyl part, the substituents in the phenyl part in the last three cases being selected from halogen, cyano, nitro and alkyl and alkoxy with in either case 1 to 2 carbon atoms, or R represents alkylamino with 1 to 12 carbon atoms, dialkylamino with 1 to 4 carbon atoms in each alkyl part, halogenoalkylamino with up to 4 carbon atoms and up to 5 identical or different halogen atoms, alkoxycarbonylamino with 1 to 4 carbon atoms in the alkyl part, alkoxyalkylamino with 1 to 4 carbon atoms in each alkyl part or optionally monosubstituted or polysubstituted phenylamino, the substituents being selected from halogen, nitro, cyano, straight-chain or branched alkyl with 1 to 4 carbon atoms, alkoxy or alkylthio with in either case 1 or 2 carbon atoms and up to 5 identical or different halogen atoms and alkoxycarbonylalkenyl with 1 to 4 carbon atoms in the alkyl part and 2 to 4 carbon atoms in the alkenyl part,
X represents hydrogen or fluorine,
Z represents halogen, cyano, nitro, straight-chain or branched alkyl with up to 4 carbon atoms, cycloalkyl with 5 to 7 carbon atoms, halogenoalkyl with up to 2 carbon atoms and up to 5 halogen atoms, alkoxycarbonyl with a total of up to 5 carbon atoms, alkoxy or alkylthio with in either case up to 2 carbon atoms or optionally substituted phenyl or phenoxy, the substituents being selected from halogen, amino, cyano, nitro and alkyl with 1 to 2 carbon atoms, or Z represents optionally substituted phenylalkyl with 1 to 2 carbon atoms in the alkyl part, the substituent in the alkyl part being alkylcarbonyloxy with a total of up to 3 carbon atoms, and each substituent in the phenyl part being halogen, nitro or cyano, and n represents 0, 1, 2, 3, 4 or 5, or an acid addition salt with a hydrogen halide acid, phosphoric acid, nitric acid, sulphuric acid, a sulphonic acid or a monofunctional or bifunctional carboxylic or hydroxycarboxylic acid, or a complex thereof with a metal salt, of which the metal is copper, zinc, manganese, magnesium, tin, iron or nickel and of which the anion is halide, nitrate, sulphate or phosphate.

2. A compound according to claim 1, wherein such compound is 2-acetoxy-3,3-bisfluoromethyl-1-(4-chlorophenoxy)-1-(imidazol-1-yl)-butane of the formula

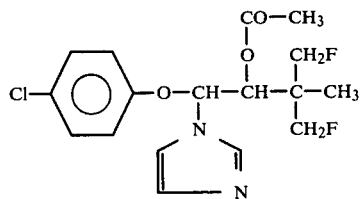

or an acid addition salt or metal salt complex thereof.

3. A compound according to claim 1, wherein such compound is 2-acetoxy-1-(2,4-dichlorophenoxy)-3,3-dimethyl-4-fluoro-1-(imidazol-1-yl)-butane of the formula

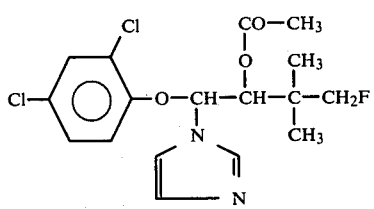

or an acid addition salt or metal salt complex thereof.

4. A compound according to claim 1, wherein such compound is 2-acetoxy-3,3-bisfluoromethyl-1-(4-fluorophenoxy)-1-(imidazol-1-yl)-butane of the formula

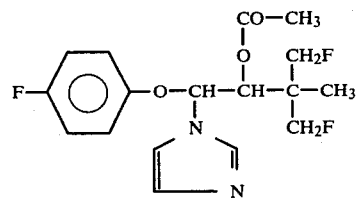

or an acid addition salt or metal salt complex thereof.

5. A compound according to claim 1, wherein such compound is 2-acetoxy-3,3-bisfluoromethyl-1-(4-chlorophenoxy)-1-(imidazol-1-yl)-butane of the formula

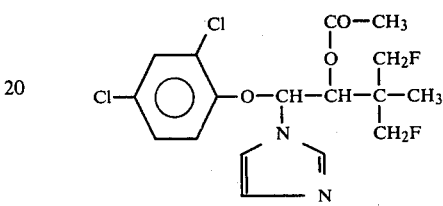

or an acid addition salt or metal salt complex thereof.

6. A fungicidal composition containing as active ingredient a fungicidally effective amount of a compound, salt or complex according to claim 1 in admixture with a diluent.

7. A method of combating fungi comprising applying to the fungi, or to a habitat thereof, a fungicidally effective amount of a compound, salt or complex according to claim 1.

8. The method accordig to claim 7, wherein the compound is 2-acetoxy-3,3-bisfluoromethyl-1-(4-chlorophenoxy)-1-(imidazol-1-yl)-butane, 2-acetoxy-1-(2,4-dichlorophenoxy)-3,3-dimethyl-4-fluoro-1-(imidazol-1-yl)butane, 2-acetoxy-3,3-bisfluoromethyl-1-(4-fluorophenoxy)-1-(imidazol-1-yl)-butane or 2-acetoxy-3,3-bisfluoromethyl-1-(2,4-dichlorophenoxy)-1-(imidazol-1-yl)-butane.

* * * * *